United States Patent
Nakagawa et al.

(10) Patent No.: US 9,562,231 B2
(45) Date of Patent: Feb. 7, 2017

(54) THERAPEUTIC AGENT FOR CORNEAL EPITHELIAL DISORDER

(71) Applicant: SENJU PHARMACEUTICAL CO., LTD., Osaka-shi, Osaka (JP)

(72) Inventors: Ayumi Nakagawa, Kobe (JP); Takeshi Nakajima, Kobe (JP); Mitsuyoshi Azuma, Kobe (JP)

(73) Assignee: Senju Pharmaceutical Co., Ltd., Osaka-shi (JP)

( * ) Notice: Subject to any disclaimer, the term of this patent is extended or adjusted under 35 U.S.C. 154(b) by 0 days.

(21) Appl. No.: 14/914,962

(22) PCT Filed: Aug. 27, 2014

(86) PCT No.: PCT/JP2014/072484
§ 371 (c)(1),
(2) Date: Feb. 26, 2016

(87) PCT Pub. No.: WO2015/030078
PCT Pub. Date: Mar. 5, 2015

(65) Prior Publication Data
US 2016/0208250 A1  Jul. 21, 2016

(30) Foreign Application Priority Data
Aug. 28, 2013  (JP) .................. 2013-176996

(51) Int. Cl.
| | |
|---|---|
| C07H 21/02 | (2006.01) |
| C07H 21/04 | (2006.01) |
| C12N 15/11 | (2006.01) |
| A61K 48/00 | (2006.01) |
| C12N 15/113 | (2010.01) |
| C12N 5/079 | (2010.01) |

(52) U.S. Cl.
CPC ......... *C12N 15/113* (2013.01); *C12N 5/0621* (2013.01); *C12N 2310/113* (2013.01); *C12N 2310/3231* (2013.01); *C12N 2320/30* (2013.01); *C12N 2501/65* (2013.01)

(58) Field of Classification Search
None
See application file for complete search history.

(56) References Cited

U.S. PATENT DOCUMENTS

| | | |
|---|---|---|
| 2005/0182005 A1 | 8/2005 | Tuschl et al. |
| 2010/0183587 A1 | 7/2010 | Dana et al. |
| 2011/0190372 A1* | 8/2011 | Tomic-Canic ....... C12N 15/113 514/44 A |
| 2014/0080894 A1 | 3/2014 | Mcelligott |
| 2014/0221456 A1 | 8/2014 | Schwob et al. |

FOREIGN PATENT DOCUMENTS

| | | |
|---|---|---|
| JP | 2012-515164 A | 7/2012 |
| KR | 10-2013-0000038 A | 1/2013 |
| WO | WO 2011/034207 A1 | 3/2011 |
| WO | WO 2012/119051 A2 | 9/2012 |
| WO | WO 2012/166646 A1 | 12/2012 |

OTHER PUBLICATIONS

Viticchie et al (Cell Death and Disease (2012) 3, e435, published Nov. 29, 2012).*
Yi et al (Nature, 452:225-229 (2008) and supplementary material).*
Lena et al (Cell Death Differ., 15:1187-1195 (2008)).*
Horwich et al (Nature Protocols 2(10): 1537-1549, 2008).*
Fabiani et al (Experimental Eye Research 89 (2009) 166-171).*
Nishida et al (American Journal of Pathology, vol. 154(2): 331-336, 1999).*
Extended European Search Report, dated Oct. 14, 2016, for European Application No. 14840320.7.
Nakagawa et al., "miRNA-203 regulates proliferation in cultured human corneal epithelial cells", IOVS, vol. 56, No. 7, Jun. 2015, p. 5481.
International Search Report, issued Nov. 25, 2014, for International Application No. PCT/JP2014/072484.
Jin et al., "The Expression and Function of microRNA-203 in Lung Cancer," Tumor Biol., vol. 34, No. 1, 2013 (Published online Oct. 17, 2012), pp. 349-357.
Malek et al., "Selection of Optimal Combinations of Target Genes for Therapeutic Multi-gene Silencing Based on miRNA Co-regulation," Cancer Gene Therapy, vol. 20, Published Online Apr. 26, 2013, pp. 326-329.
Nissan et al., "miR-203 Modulates Epithelial Differentiation of Human Embryonic Stem Cells towards Epidermal Stratification," Developmental Biology, vol. 356, No. 2, Available Online Jun. 12, 2011, pp. 506-515.

(Continued)

*Primary Examiner* — Richard Schnizer
(74) *Attorney, Agent, or Firm* — Birch, Stewart, Kolasch & Birch, LLP

(57) ABSTRACT

A therapeutic agent for a corneal epithelial disorder, containing a miR-203 inhibitor; an agent for promoting proliferation of corneal epithelial cells, containing a miR-203 inhibitor; a liquid culture medium for use in the manufacture of a corneal epithelial sheet, containing a miR-203 inhibitor; and a method for producing a corneal epithelial sheet, including the step of culturing corneal epithelial cells using a liquid culture medium containing a miR-203 inhibitor. According to the present invention, a therapeutic agent for a corneal epithelial disorder, an agent for promoting proliferation of corneal epithelial cells, a liquid culture medium for use in the manufacture of a corneal epithelial sheet, a method for producing a corneal epithelial sheet, including the step of culturing corneal epithelial cells using the liquid culture medium, and a method for treating a corneal epithelial disorder can be provided. The present inventors have also found that not only the above effects are exhibited by inhibiting miRNA richly contained in tears, but also the agent specifically acts on eye surfaces, so that the present invention can be expected to show high safety.

13 Claims, 4 Drawing Sheets

(56) References Cited

OTHER PUBLICATIONS

Sonkoly et al., "MicroRNAs: Novel Regulators Involved in the Pathogenesis of Psoriasis?," PLoS ONE, vol. 2, No. 7, e610, Jul. 2007, pp. 1-8.

Takeshita et al., "miR-203 Inhibits the Migration and Invasion of Esophageal Squamous Cell Carcinoma by Regulating LASP1," International Journal of Oncology, vol. 41, No. 5, 2012, pp. 1653-1661.

Zhao et al., "Estrogen Receptor-mediated Regulation of MicroRNA Inhibits Proliferation of Vascular Smooth Muscle Cells," Arterioscler Thromb Vasc Biol., vol. 33, No. 2, Feb. 2013, pp. 257-265 (Total 23 pages).

* cited by examiner (a)

(b)

*:P<0.05

THERAPEUTIC AGENT FOR CORNEAL EPITHELIAL DISORDER

TECHNICAL FIELD

The present invention relates to a therapeutic agent for a corneal epithelial disorder, containing a miR-203 inhibitor. Further, the present invention relates to an agent for promoting proliferation of corneal epithelial cells, containing a miR-203 inhibitor. Further, the present invention relates to a liquid culture medium for use in the manufacture of a corneal epithelial sheet, containing a miR-203 inhibitor. Further, the present invention relates to a method for producing a corneal epithelial sheet, including the step of culturing corneal epithelial cells using a liquid culture medium containing a miR-203 inhibitor. Further, the present invention relates to a method for treating a corneal epithelial disorder using a miR-203 inhibitor.

BACKGROUND ART

Corneal epithelial disorders have been posing some problems as symptoms of ophthalmic diseases caused by progression of dry eye or an inappropriate use of contact lenses.

On the other hand, microRNA (miRNA) is a noncoding RNA of 25 nucleotides or so in length that does not contain genetic information, and has a role of binding with messenger RNA (mRNA) within a cell to inhibit the translation to a protein. It has been elucidated that a single kind of miRNA suppresses expression of plural target mRNAs, and that a single kind of mRNA is controlled by plural miRNAs. Further, it has been expected that at least 30% of human genes, or more of gene expressions is controlled by these miRNAs.

In the recent years, a large number of reports have been made on the involvement of miRNA in suppression of cancer or natural immunoreactions, so that the importance of its role is even more remarked. In addition, it has been found that miRNA not only functions in the expressed cells but also is included in membrane vesicles called exosomes to be exported from the cells and transported to other cells through body fluids, so that the translation of mRNA to a protein is also inhibited in the same manner in other cells.

miR-203 is miRNA that is found to be expressed highly in skin, and suggested to be involved in regulation of epidermal differentiation, formation of barrier functions of skin and skin diseases such as psoriasis (Non-Patent Publication 1). miR-203 reportedly has a function as a suppressive factor for cancer or tumors (Non-Patent Publications 2 and 3). In addition, miR-203 reportedly acts to suppress proliferation of vascular smooth muscle cells but not to suppress proliferation of venal epithelial cells of human umbilical chords (Non-Patent Publication 4). However, as far as we know, there are no reports that suggest the associations between corneal epithelial cells and miR-203 at all.

PRIOR ART REFERENCES

Non-Patent Publications

Non-Patent Publication 1: Sonkoly E et. al., MicroRNAs: Novel regulators involved in the pathogenesis of psoriasis?, *PLoS ONE*, (2007), 2(7), e610

Non-Patent Publication 2: Jin J et. al., The expression and function of microRNA-203 in lung cancer, *Tumour Biol*, (2013), 34(1), 349-57

Non-Patent Publication 3: Takeshita N et. al., miR-203 inhibits the migration and invasion of esophageal squamous cell carcinoma by regulating LASP1, *Int J Oncol*, (2012), 41(5), 1653-61.

Non-Patent Publication 4: Zhao J et. al., Estrogen Receptor-Mediated Regulation of MicroRNA Inhibits Proliferation of Vascular Smooth Muscle Cells, *Arterioscler Thromb Vasc Biol*, (2013), 33(2), 257-65

SUMMARY OF THE INVENTION

Problems to be Solved by the Invention

Therefore, an object of the present invention is to provide a therapeutic agent for a corneal epithelial disorder, having an action of promoting proliferation of corneal epithelial cells. Further, an object of the present invention is to provide an agent for promoting proliferation of corneal epithelial cells. Further, an object of the present invention is to provide a liquid culture medium for use in the manufacture of a corneal epithelial sheet. Further, an object of the present invention is to provide a method for producing a corneal epithelial sheet. Further, an object of the present invention is to provide a method for treating a corneal epithelial disorder.

Means to Solve the Problems

As a result of intensive studies in order to solve the above-mentioned problems, the present inventors have found that miRNA richly contained in tears is present, as compared to sera of monkeys, and when the miRNA is identified, one of the miRNA is found to specifically suppress proliferation of corneal epithelial cells, and further that an inhibitor for this miRNA has an action of promoting proliferation of corneal epithelial cells. The present invention has been perfected based on these findings.

Concretely, the gist of the present invention relates to:

[1] a therapeutic agent for a corneal epithelial disorder, containing a miR-203 inhibitor;

[2] an agent for promoting proliferation of corneal epithelial cells, containing a miR-203 inhibitor;

[3] a liquid culture medium for use in the manufacture of a corneal epithelial sheet, containing a miR-203 inhibitor;

[4] a method for producing a corneal epithelial sheet, including the step of culturing corneal epithelial cells using a liquid culture medium containing a miR-203 inhibitor;

[5] a method for treating a corneal epithelial disorder, including the step of administering a substance that inhibits an action of miR-203, for example, a miR-203 inhibitor, to an individual in need of treatment of a corneal epithelial disorder in a therapeutically effective amount;

[6] a substance that inhibits the action of miR-203, for use in the treatment of a corneal epithelial disorder, for example, a miR-203 inhibitor;

[7] a method for promoting proliferation of corneal epithelial cells, including:
administering a substance that inhibits an action of miR-203, for example, a miR-203 inhibitor, to an individual in need of promoting proliferation of corneal epithelial cells in an effective amount, or
adding the substance to a liquid culture medium for culturing the cells in an effective amount; and

[8] a substance that inhibits an action of miR-203 for use in promoting proliferation of corneal epithelial cells, for example, a miR-203 inhibitor.

Effects of the Invention

According to the present invention, a therapeutic agent for a corneal epithelial disorder, an agent for promoting proliferation of corneal epithelial cells, a liquid culture medium for use in the manufacture of a corneal epithelial sheet, a method for producing a corneal epithelial sheet including the step of culturing corneal epithelial cells using the liquid culture medium, and a method for treating a corneal epithelial disorder can be provided. The present inventors have found that not only the above effects are exhibited by inhibiting miRNA richly contained in tears, but also the agent specifically acts on eye surfaces, so that the present invention can be expected to show high safety.

Figure 1:
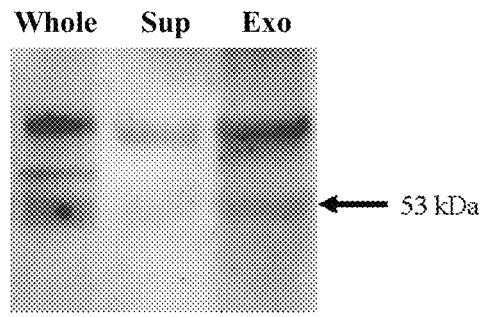
FIG. 1 is an electrophoretic image showing the detection of exosome in tears according to a western blot method using an anti-CD63 antibody. A marker protein of exosome, CD63 (molecular weight: 53 kDa) was detected by a western blot method, wherein whole: whole fractions for monkey tears, Sup: a supernatant fraction, and Exo: an exosomal fraction.

MODES FOR CARRYING OUT THE INVENTION 1. miR-203 and miR-203 Inhibitor miR-203 as used herein is one kind of miRNAs, which is a single-stranded RNA having a nucleotide sequence consisting of 22 nucleotides as shown in SEQ ID NO: 1 of the Sequence Listing. The present inventors have conducted experiments using a miR-203 inhibitor capable of inhibiting the action of miR-203, as shown in Test Examples given later, and found that the miR-203 inhibitor has an action of promoting proliferation of human corneal epithelial cells.

The miR-203 inhibitor as used herein is not particularly limited so long as the inhibitor has the function of inhibiting an action of miR-203. Preferred examples of the miR-203 inhibitor include an antisense nucleic acid against miR-203, and a polynucleotide having a nucleotide sequence complementary to the nucleotide sequence of miR-203 can be used.

The phrase "antisense nucleic acid against miR-203" in the present invention refers to a nucleic acid containing a nucleotide sequence or a part thereof, which is complementary or substantially complementary to the nucleotide sequence of miR-203 which is a target nucleic acid, the nucleic acid hybridizing to at least a part of the nucleotide sequence of miR-203, and having the function of suppressing an action of miR-203. The phrase "substantially complementary" as used herein intends to embrace partial mismatches, so long as a nucleic acid hybridizes at a target site, and is capable of suppressing an action of miR-203. Concretely, the "substantially complementary" sequence refers to a sequence having a complementarity of 70% or more, preferably 80% or more, more preferably 90% or more, and even more preferably 95% or more, based on the sequence of the target site. The antisense nucleic acid may be DNA or RNA, which may be single-stranded or double-stranded. The number of nucleotides is preferably from 5 to 50, more preferably from 6 to 24, even more preferably 7 to 23, and especially preferably from 8 to 22, from the viewpoint of the action and properties as the antisense.

One example of the preferred embodiments of the antisense nucleic acid against miR-203 includes an RNA containing a nucleotide sequence as shown in SEQ ID NO: 2 of the Sequence Listing having a nucleotide sequence 100% complementary to SEQ ID NO: 1 of the Sequence Listing. Other preferred embodiments of the preferred embodiments of the antisense nucleic acid against miR-203 include an RNA containing a part of a nucleotide sequence as shown in SEQ ID NO: 2 of the Sequence Listing, for example, an RNA containing a sequence of positions 2 to 21 of SEQ ID NO: 2 of the Sequence Listing (SEQ ID NO: 3 of the Sequence Listing); an RNA containing a sequence of positions 7 to 22 of SEQ ID NO: 2 of the Sequence Listing (SEQ ID NO: 4 of the Sequence Listing); and an RNA containing a sequence of positions 14 to 21 of SEQ ID NO: 2 of the Sequence Listing (SEQ ID NO: 5 of the Sequence Listing). Other preferred embodiments of antisense nucleic acids against miR-203 include an RNA indispensably containing a nucleotide sequence as shown in SEQ ID NO: 5 of the Sequence Listing, wherein one to thirteen nucleotides are added to a 5'-side of the RNA and/or one nucleotide is added to a 3'-side. Here, the kinds of the nucleotides added to a 5'-side are more preferably the same as the kinds of nucleotides constituting first to thirteenth positions of the nucleotide sequence as shown in SEQ ID NO: 2 of the Sequence Listing. Here, a firstly added nucleotide is a thirteenth-position nucleotide, i.e. adenine, the next added nucleotide is a twelfth-position nucleotide, i.e. adenine, and nucleotides can be subsequently added in the order of eleventh to first-positions. In addition, the kind of the nucleotide added to a 3'-side is more preferably a twenty-second position of the nucleotide sequence as shown in SEQ ID NO: 2 of the Sequence Listing, i.e. cytosine.

More preferred embodiments of the antisense nucleic acids as mentioned above include an RNA consisting of a nucleotide sequence having substitution, deletion, addition and/or insertion of one to several nucleotides, for example, one to three nucleotides, and preferably one or two nucleotides, in the nucleotide sequence as shown in any one of SEQ ID NOs: 2 to 5 of the Sequence Listing. Even more preferred embodiments include an RNA consisting of a nucleotide sequence having substitution and/or deletion of one nucleotide of 5'-terminal and/or one nucleotide of 3'-terminal of the nucleotide sequence, in the nucleotide sequence as shown in any one of SEQ ID NOs: 2 to 5 of the Sequence Listing; and an RNA consisting of a nucleotide sequence having addition of one nucleotide to a nucleotide at a 5'-terminal and/or to a nucleotide at a 3'-terminal of the nucleotide sequence. In the RNAs having a mutation in the sequence as mentioned above, it is more preferred to have an action of promoting proliferation of corneal epithelial cells.

Even more preferred embodiments of antisense nucleic acids as mentioned above include an RNA consisting of a nucleotide sequence as shown in SEQ ID NO: 2 of the Sequence Listing; an RNA consisting of a nucleotide sequence as shown in SEQ ID NO: 3 of the Sequence Listing; an RNA consisting of a nucleotide sequence as shown in SEQ ID NO: 4 of the Sequence Listing; and an RNA consisting of a nucleotide sequence as shown in SEQ ID NO: 5 of the Sequence Listing. Here, the phrase "RNA having an action of promoting proliferation of corneal epithelial cells" as used herein refers to an RNA having an action of increasing cell counts more significantly than the cell counts of the corneal epithelial cells in a case of treating with a negative control in the methods shown in Test Examples 5 and 6 set forth below.

The antisense nucleic acid against miR-203 may be modified by a protective group or the like which is ordinarily used so long as the antisense nucleic acid has an action of promoting proliferation of corneal epithelial cells. In other words, the term "antisense nucleic acid" as used herein embraces both the embodiments of those modified by a protective group or the like, and those without a modification by a protective group or the like. The modified nucleic acid includes a nucleic acid having substitution of a hydroxyl group at 2'-position of the sugar moiety of the nucleic acid with a methoxy group, a nucleic acid in which an oxygen atom at 2'-position and a carbon atom at 4'-position are bridged via a methylene, and the like. More concretely, in a case where the antisense nucleic acid is an RNA, an RNA having substitution of at least one hydroxyl group at 2'-position of a ribonucleic acid constituting the RNA with a methoxy group is preferred, and an RNA having substitutions of all the hydroxyl groups with methoxy groups is more preferred, from the viewpoint of stability as RNA and efficiency of introduction into cells. In other concrete examples, an RNA in which an oxygen atom at 2'-position and a carbon atom at 4'-position of at least one ribonucleic acid constituting the RNA are bridged via a methylene as shown in the following formula is more preferred.

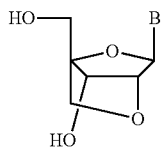

The polynucleotide accompanying a modification as mentioned above has an effect of promoting proliferation of corneal epithelial cells that is of the same level as an antisense polynucleotide without a modification against miR-203.

As the polynucleotide having a nucleotide sequence complementary to a nucleotide sequence of miR-203, the polynucleotide can be synthesized by a known method, or a commercially available product can be utilized. Concrete examples of commercially available products include miScript miRNA Inhibitor Anti-hsa-miR-203(trade name) of QIAGEN, and miRCURY LNA microRNA Inhibitors(trade name) of EXIQON. This miScript miRNA Inhibitor Anti-hsa-miR-203 is an RNA having a nucleotide sequence as shown in SEQ ID NO: 2 of the Sequence Listing, having substitutions of hydroxyl groups at 2'-position of all the ribonucleic acids constituting the RNA with methoxy groups.

2. Agent for Promoting Proliferation of Corneal Epithelial Cells

The miR-203 inhibitor mentioned above has an action of promoting proliferation of corneal epithelial cells, so that the inhibitor can be utilized as an agent for promoting proliferation of corneal epithelial cells. The agent for promotion is used in vivo or in vitro as a medicament or a reagent or the like. When the agent is used as a medicament, the agent can be applied as a therapeutic agent for a disease accompanying injuries (in other words, wounds or defects) on corneal epithelial cells. When the agent is used as a reagent, the agent can be blended in a liquid culture medium for producing a corneal epithelial sheet.

3. Therapeutic Agent for Corneal Epithelial Disorder

The miR-203 inhibitor mentioned above has an action of promoting proliferation of corneal epithelial cells, so that the miR-203 inhibitor can be applied as a therapeutic agent for a corneal epithelial disorder, and the therapeutic agent for a corneal epithelial disorder containing a miR-203 inhibitor as mentioned above is embraced by the present invention.

Corneal epithelium is supplemented by proliferation of corneal basal cells and lasting supply of epithelial cells from limbus epithelium, and on the other hand, turnovers of corneal epithelium are repeated in a short period of time by desquamation of outermost cells. It has been known that the homeostasis balance of the epithelium is lost, so that onset of a corneal epithelial disorder takes place, if epithelial proliferation ability is suppressed, or desquamation is promoted by some pathologies (edited by Shigeru Kinoshita (2005). "*Kakumaku Shikkan Gairaide Koumite Kounaose (How to Diagnose or Treat Out-Patients with Corneal Diseases)*," published by K.K. Medical Review, pages 82-85).

The wound healing of a corneal epithelial disorder is considered to take place in three steps shown as follows: Concretely, cell migration for covering a defective region, subsequent cell proliferation for supplementing deficient cells, and formation of cell layers by overlaid layers of cells. Regarding the cell proliferation, it has been already reported that epidermal growth factor (EGF), platelet-derived growth factor (PDGF), and keratinocyte growth factor (KGF) promote proliferation of corneal epithelial cells, and these growth factors are produced in corneal epithelial cells, so that the importance of cell proliferation in wound healing is shown (Agrawal V B, Tsai R J, Corneal epithelial wound healing. *Indian J Ophthalmol* 2003; 51: 5-15 and *Exp Biol Med* 226(7): 653-664, 2001). Further, recently, it has been reported that pigment epithelium-derived factor (PEDF) also plays an important role in proliferation of corneal cells in the process of wound healing (Stem Cells. 2013 Apr. 3. doi: 10.1002/stem.1393). Therefore, promotion of proliferation of corneal epithelial cells is useful as a method for treatment of a corneal epithelial disorder, so that once a certain component is acknowledged to have an action of promoting proliferation of corneal epithelial cells in an in vitro experimentation system, one of ordinary skill in the art can expect to use the component as a therapeutic agent for a corneal epithelial disorder, or can expect a method for treating a corneal epithelial disorder utilizing the component.

Since the therapeutic agent of the present invention has an action of promoting proliferation of corneal epithelial cells, the agent is useful as a therapeutic agent for a corneal epithelial disorder. The corneal epithelial disorder refers to a disease accompanying an injury (in other words, wound or defect) of corneal epithelial cells. Concretely, the therapeutic agent of the present invention is useful as a therapeutic agent of a corneal epithelial disorder accompanying Sjögren syndrome, Stephens-Johnson syndrome, keratoconjunctivitis sicca (dry eye), diabetic keratopathy, post-operation, drug use, trauma, corneal ulcer, meibomianitis, symptoms caused while wearing contact lenses, vernal catarrh, atopic keratoconjunctivitis, superficial punctate keratitis, corneal epithelial erosion, or the like. Further, the therapeutic agent of the present invention is also useful as an agent for promoting corneal wound healing.

The therapeutic agent of the present invention can be applied to a mammal. The mammal as used herein includes primates (e.g. human, monkey), bovine, sheep, goats, horses, dogs, cats, rabbits, guinea pigs, rats, mice, and the like.

In the therapeutic agent of the present invention, the dose of the miR-203 inhibitor can be appropriately selected depending upon the symptoms, ages, dosage forms, and the like. As described later, the miRNA inhibitor shows an effect of promoting proliferation of human corneal epithelial cells even at a low concentration of 50 nM or 100 nM, so that a clinical physician may set a dose of the miR-203 inhibitor appropriately, based on the concentration. As one example, the therapeutically effective amount of the eye drops, in terms of the concentration of the miR-203 inhibitor, is such that an agent with a dose of preferably from 0.00001 to 1% (w/v), and more preferably from 0.001 to 0.1% (w/v) may be dropped one to four times a day.

The therapeutic agent of the present invention can be administered orally, or parenterally (in eye drops, transdermally, or the like). The dosage form includes eye drops, ophthalmic ointments, skin ointments, injections, tablets, capsules, granules, fine powders, powder, and the like. These therapeutic agents can be prepared using well used techniques. For example, eye drops can be prepared by optionally using an isotonic agent such as sodium chloride or a concentrated glycerol, a buffer such as sodium phosphate or sodium acetate, a surfactant such as polyoxyethylene sorbitan monooleate, Polyoxyl 40 Stearate, or polyoxyethylene hydrogenated castor oil, a stabilizer such as sodium citrate or sodium edetate, a preservative such as benzalkonium chloride or Parabene, or the like. A preferred solvent used in eye drops is purified water. The pH in a case of use as eye drops may be within the range acceptable to the eye drop, and it is preferably within the range of from 4 to 8.

The ophthalmic ointment can be prepared by using a widely used basal agent such as white Vaseline or a liquid paraffin. In addition, an oral preparation in the forms of tablets, capsules, granules, fine powders, powders or the like can be prepared by optionally adding an extender such as lactose, crystalline cellulose, starch, or vegetable oil, a lubricant such as magnesium stearate or talc, a binder such as hydroxypropyl cellulose or polyvinyl pyrrolidone, a disintegrant such as carboxymethyl cellulose calcium or low-substituted hydroxypropyl methyl cellulose, a coating agent such as hydroxypropyl methyl cellulose, macrogol or a silicone resin, a film-forming agent for a gelatin film, or the like.

4. Corneal Epithelial Sheet

Since the above miR-203 inhibitor promotes proliferation of corneal epithelial cells, the corneal epithelial cells can be efficiently cultured by blending the inhibitor in a liquid culture medium. Accordingly, a liquid culture medium for the manufacture of a corneal epithelial sheet, containing a miR-203 inhibitor as described above, a method for producing a corneal epithelial sheet including the step of culturing corneal epithelial cells using the liquid culture medium, and a corneal epithelial sheet produced by the method are also embraced in the present invention.

The concentration of the miR-203 inhibitor in the liquid culture medium of the present invention is not particularly limited, and the concentration is, for example, preferably within the range of from 0.01 to 1,000 nM, and more preferably within the range of from 1 to 200 nM. The preferred embodiment of the liquid culture medium of the present invention includes a liquid culture medium prepared by adding the above miR-203 inhibitor to a known medium used in the field of cell culture. The known medium includes DMEM/F12 (Invitrogen), OcuLife (registered trademark) BM (Kurabo), and the like. The liquid culture medium of the present invention may contain a known component used in the field of cell culture, for example, an inorganic salt (sodium chloride, potassium chloride, calcium chloride, etc.), an organic salt, amino acids, a buffer, vitamin, serum, or an antibiotic.

As a method for producing a corneal epithelial sheet, for example, culturing is carried out using a liquid culture medium containing a miR-203 inhibitor, during the production of a corneal epithelial sheet described in the method for production of Japanese Unexamined Patent Publication No. 2006-003818, whereby proliferation of corneal epithelial cells is promoted, and a corneal epithelial sheet can be produced in a short period of time.

5. Method for Treating Corneal Epithelial Disorder of the Present Invention

The present invention provides a method for treating a corneal epithelial disorder, including the step of administering a substance that inhibits an action of miR-203, for example, a miR-203 inhibitor, in a therapeutically effective amount, to an individual in need of treatment of a corneal epithelial disorder.

The individual in need of treatment of a corneal epithelial disorder as used herein is preferably human, but the individual may also be primates other than human (for example, monkey), bovine, sheep, goat, horse, dog, cat, rabbit, guinea pig, rat, mice, and the like.

The therapeutically effective amount as used herein refers to an amount of treating or relieving a corneal epithelial disorder in a case where a substance that inhibits an action of miR-203 is administered to the above individual, as compared to an individual not administered.

A concrete effective amount is appropriately set depending upon dosage forms, methods of administration, purposes of use, and age, body weight, symptoms or the like of individuals, and is not unconditionally determined. In one example, a therapeutically effective amount of eye drops is an amount accomplished by dropping, in terms of the concentration of the substance that inhibits an action of miR-203, preferably from 0.00001 to 1% (w/v), and more preferably from 0.001 to 0.1% (w/v) for once to four times a day.

In the method for treatment of the present invention, a substance that inhibits an action of miR-203 may be directly administered to the above individual, or may be administered as a pharmaceutical such as a therapeutic agent for a corneal epithelial disorder as mentioned above, for example, eye drops or ophthalmic ointment, so as to be in a therapeutically effective amount mentioned above. The method of administration is not particularly limited, and for example, the substance can be administered orally or parenterally (in eye drops, transdermally, etc.).

According to the method for treating a corneal epithelial disorder of the present invention, the corneal epithelial disorder can be treated or relieved by the above effects exhibited by the substance that inhibits an action of miR-203. Preferred examples of the substance that inhibits an action of miR-203 include, for example, a miR-203 inhibitor mentioned above.

Further, the present invention embraces a substance that inhibits an action of miR-203, for use in treatment of a corneal epithelial disorder, for example, a miR-203 inhibitor.

6. Method for Promoting Proliferation of Corneal Epithelial Cells of the Present Invention The present invention provides a method for promoting proliferation of corneal epithelial cells, including the steps of (1) administering to an individual in need of promotion of proliferation of corneal epithelial cells, or (2) adding to a liquid culture medium for culturing the corneal epithelial cells, a substance that inhibits an action of miR-203, for example, a miR-203 inhibitor, in an effective amount.

The individual in need of promoting proliferation of corneal epithelial cells as used herein is preferably human, but the individual may also be primates other than human (for example, monkey), bovine, sheep, goat, horse, dog, cat, rabbit, guinea pig, rat, mice, and the like.

The effective amount as used herein refers to either an amount that can promote proliferation of corneal epithelial cells as compared to an individual not administered, in a case where a substance that inhibits an action of miR-203 is administered to the above individual, or an amount that can promote proliferation of corneal epithelial cells as compared to a case where the cells are cultured without adding the substance, in a case where the substance that inhibits an action of miR-203 is added to a liquid culture medium for culturing corneal epithelial cells. A concrete effective amount is appropriately set depending upon dosage forms, methods of administration, purposes of use, and age, body weight, symptoms or the like of individuals, and is not unconditionally determined. In one example, an effective amount when used as eye drops is an amount accomplished by dropping, in terms of the concentration of the substance that inhibits an action of miR-203, preferably from 0.00001 to 1% (w/v), and more preferably from 0.001 to 0.1% (w/v) for once to four times a day. Alternatively, the concentration of the substance when the substance that inhibits an action of miR-203 is added to a liquid culture medium is preferably within the range of from 0.01 to 1,000 nM, and more preferably within the range of from 1 to 200 nM.

In the method for promotion of the present invention, a substance that inhibits an action of miR-203 may be directly administered to the above individual, or may be added to a liquid culture medium, so as to be in an effective amount mentioned above. Alternatively, the substance may be administered as a pharmaceutical such as a therapeutic agent for a corneal epithelial disorder as mentioned above, for example, eye drops or ophthalmic ointment. The method of administration is not particularly limited, and for example, the substance can be administered orally or parenterally (in eye drops, transdermally, etc.).

According to the method for promoting proliferation of corneal epithelial cells of the present invention, proliferation of the corneal epithelial cells can be efficiently promoted by the above effects exhibited by the substance that inhibits an action of miR-203. Preferred examples of the substance that inhibits an action of miR-203 include, for example, a miR-203 inhibitor mentioned above.

Further, the present invention embraces a substance that inhibits an action of miR-203, for example, a miR-203 inhibitor, for use in promoting proliferation of corneal epithelial cells.

EXAMPLES

The present invention will be hereinbelow described based on Test Examples and Formulation Examples, without intending to limit the present invention to these Test Examples and the like.

Test Example 1

Isolation of Exosomes in Tears and Sera of Monkey

Tears and sera of monkey (scientific name: *Macaca fascicularis*) were collected, and respectively centrifuged at 3,000×g for 15 minutes, to remove cell components. The supernatant was collected, ExoQuick Exosome Precipitation Solution (System Biosciences) was added thereto in an equivolume, and the mixture was thoroughly mixed. The mixed solution was allowed to stand at 4° C. for 12 hours or more, and then centrifuged at 1500×g for 30 minutes. The supernatant is referred to as a supernatant fraction (Sup), and the supernatant was completely removed, and one prepared by redissolving precipitates including exosomes in a sterilized water at a 1/10 volume of the original liquid volume is referred to as an exosomal fraction (Exo).

Test Example 2

Confirmation of Expression in Exosomes According to Western Blot Method

An exosomal fraction (2 μg) isolated from tears or sera of the monkey, obtained in Test Example 1 was dissolved in NuPAGE LDS Sample Buffer (Invitrogen) and NuPAGE Sample Reducing Agent (Invitrogen), and the mixed solution was heat-treated at 70° C. for 10 minutes. The sample was electrophoresed using NuPAGE (registered trademark) 12% Bis-Tris Gel (Invitrogen) at 200 V for 35 minutes, and separated for each molecular weight. The detection of an exosomal marker CD63 was carried out according to a Western Blot method using a peroxidase-labeled goat polyclonal anti-CD63 antibody (Santa Cruz Biotechnology, Peroxidase Labeling Kit-NH2 (Dojindo)). The peroxidase was activated with ECL Plus Western Blotting Detection Reagents (GE healthcare life sciences), and CD63 was detected with ImageQuant LAS 4000 (GE healthcare life sciences). A supernatant fraction was also treated in the same manner to confirm the presence or absence of CD63.

The detection results of CD63 in tears of the monkey (Whole), and the exosomal fraction (Exo) and the supernatant fraction (Sup) isolated from the tears of the monkey as mentioned above are shown in FIG. 1. Expression of CD63 (molecular weight: 53 kDa) was confirmed in the exosomal fraction. It was confirmed from this matter that the exosomes existing in the tears were isolated. Similar results were obtained for sera of the monkey.

Test Example 3

Exhaustive Analysis of microRNA (miRNA) in Tears and Sera According to Microarray Analysis miRNA Expression levels in exosomes isolated from tears and sera of the monkey as mentioned above were exhaustively analyzed according to a microarray method. Concretely, exosomal fractions were isolated in the same manner as above from tears and sera (2 analytes each) of the monkey. The microarray analysis was performed for miRNAs contained in the exosomal fractions obtained.

Total RNA was extracted from the exosomal fractions, and the purity and concentration of miRNAs were measured with Agilent 2100 Bioanalyzer and a spectrophotometer. miRNAs were fluorescent-labeled with Hy5 (miRCURY LNA™ microRNA Hy5 Power labeling kit, Exiqon). The Hy5-labeled miRNAs were hybridized with 3D-Gene(registered trademark) Human miRNA Oligo chips (Toray), and detected with a 3D-Gen(registered trademark) scanner. As a result, the existence of about 760 kinds of miRNAs could be confirmed. It could be seen that the expression level of miR-203 in tears was relatively higher than other miRNAs, and moreover when the tears and sera were compared, miR-203 was more abundant in the tears. Here, the nucleotide sequence of the miR-203 is as shown in SEQ ID NO: 1 of the Sequence Listing, and the nucleotide sequences of miRNAs that are already known are registered at the miRBase database microrna.sanger.ac.uk, so that the nucleotide sequences of miRNAs that are already known can be easily found.

Test Example 4

Analyses of Expression Levels of miRNAs in Tears and Sera According to Quantitative Real-Time PCR Expression levels of miR-203 in tears and sear (6 analytes each) of the monkey were analyzed by quantitative real-time PCR. Total RNA including miRNA was extracted from tears and sera of the monkey with miRNeasy Mini Kit (QIAGEN), and treated with an RNase inhibitor (SUPERase-In, Ambion), and thereafter a concentration was quantitated with Nanovue (GE healthcare).

Thereafter, total RNA (0.5 ng) was reverse-transcribed with miScript II RT Kit (QIAGEN), and further, the expression levels for miR-203 were detected with 7500 Real Time PCR system (Applied Biosystems) according to quantitative real-time PCR method using miScript SYBR Green PCR Kit (QIAGEN). As the primers, those made by QIAGEN were used. The expression levels of the tears and sera were compared, based on the data obtained.

Figure 2:
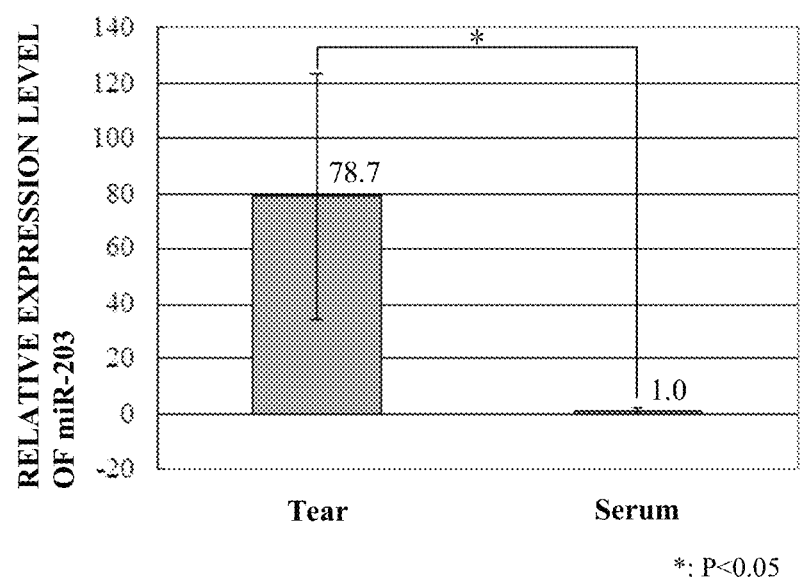
FIG. 2 is a graph showing analytical results of the expression levels of miR-203 in monkey tears and sera detected by quantitative real-time PCR. Each of data is shown by mean±standard deviation of 6 cases. Also, the results of significance test (t-test, one side, significance level 5%) are indicated (n=6).

As a result, the relative miR-203 expression levels in the tears were 78.7 times higher than the sera, and were found to have statistical significance (FIG. 2).

Test Example 5

Introduction of miR-203 Analogues and miR-203 Inhibitor into Human Corneal Epithelial Cells Human corneal epithelial cells (HCE-T (Araki-Sasaki K, Ohashi Y, Sasabe T, Hayashi K, Watanabe H, Tano Y, Handa H, *Invest Ophthalmol Vis Sci* 1995; 36:614-21.), Riken Cell Bank No. RCB2280) were seeded on a 96-well plate so as to have a density of 3.0×10³ cells/well (30-50% confluent), and pre-cultured overnight. Here, as the medium, a DMEM/F12 (Invitrogen) medium supplemented with 5 µg insulin (Wako), 10 ng/ml human recombinant EGF (Invitrogen), 5% fetal bovine serum (Invitrogen), 40 µg/mL Gentamycin (Invitrogen), and 100 U/mL penicillin/streptomycin (Invitrogen) was used.

After pre-culture, a miR-203 analogue, a miR-203 inhibitor, and negative controls thereof were diluted with the medium, the dilution was mixed with HiPerFect Transfection Reagent (QIAGEN), and the mixture was incubated at 37° C. for 10 minutes, and added to the cells. Thereafter, the cells were cultured at 37° C. for 48 hours. The miR-203 inhibitor and a negative control thereof were added to cells so as to have a concentration of 50 nM or 100 nM, and the miR-203 analogue and a negative control thereof were added to cells so as to have a concentration of 20 nM.

Here, as the miR-203 analogue, the miR-203 inhibitor, and negative controls thereof, the followings were used. Analogue Negative Control: one manufactured by QIAGEN under trade name of "AllStars Negative Control siRNA" miR-203 Analogue: one manufactured by QIAGEN under trade name of "miScript miRNA Mimic Syn-hsa-miR-203"; this is a synthetic double-stranded RNA consisting of the sequence of miR-203 and a complementary strand thereof.

Inhibitor Negative Control: one manufactured by QIAGEN under trade name of "miScript Inhibitor Negative Control" miR-203 Inhibitor: one manufactured by QIAGEN under trade name of "miScript miRNA Inhibitor Anti-hsa-miR-203"; this is a synthetic single-stranded RNA consisting of a complementary strand of a miR-203 sequence, in which hydroxyl groups at 2'-position of all the nucleic acids are substituted with methoxy groups.

Test Example 6

Determination of Live Cell Count of Human Corneal Epithelial Cells

Figure 3:
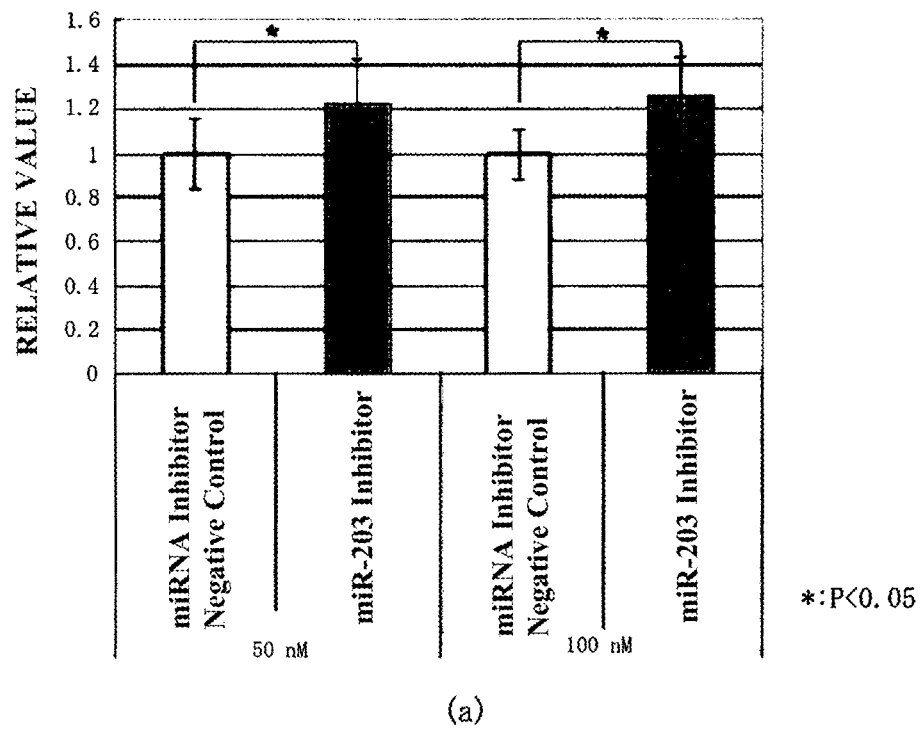
FIGS. 3(a) and (b) each is a graph showing the results of confirming the actions of each of miR-203 inhibitor and miR-203 analogues to human corneal epithelial cells (determinations of live cell counts). In addition, the results of significance test (t-test, one side, significance level: 5%) are indicated ((a) N=9, (b) N=6).
Figure 3:
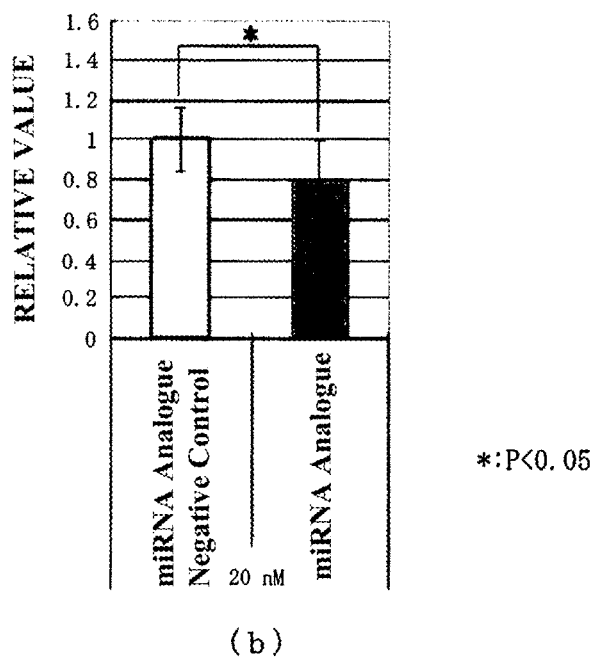

The live cell count of human corneal epithelial cells was determined with a Cell counting kit-8 (CCK-8, Dojindo). CCK-8 was added to cells cultured in Test Example 5 so as to have a final concentration of 10% (v/v), the mixture was incubated for one hour, and the absorbance at 450 nm was measured. The relative live cell count was analyzed based on the absorbance, and the results are shown in FIG. 3. In FIG. 3, the live cell count after individual tests was expressed as a relative value, when the live cell count when treated with the negative control was defined as 1. It could be seen that proliferation of the human corneal epithelial cells was significantly promoted by treating with the miR-203 inhibitor ((a) of FIG. 3), and proliferation of the cells was significantly suppressed by treating with the miR-203 analogue ((b) of FIG. 3).

Test Example 7

Figure 4:
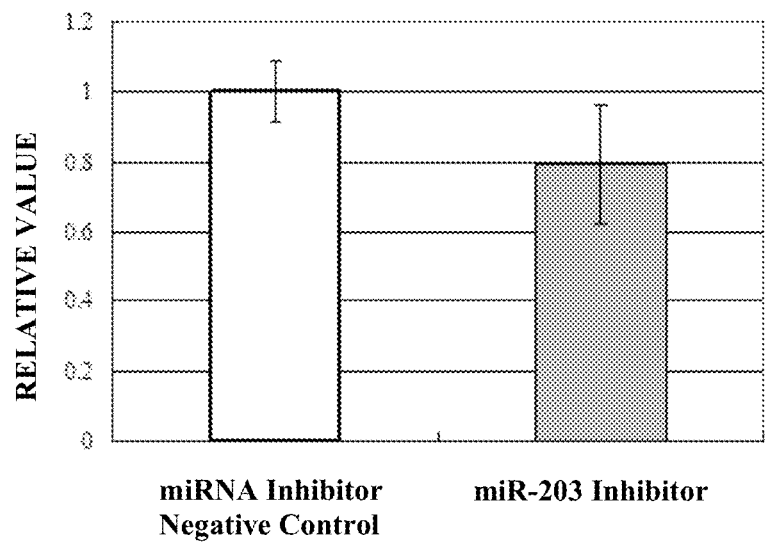
FIG. 4 is a graph showing the results confirming the action of the miR-203 inhibitor on human retinal microvascular epithelial cells (determination of live cell count) (n=3).

Introduction of miR-203 Inhibitor into Normal Human Retinal Microvascular Endothelial Cells and Determination of Live Cell Count Normal human retinal microvascular endothelial cells (CELL SYSTEMS CORPORATION, Cat No. ACBRI181) were seeded on a 96-well plate so as to have a density of 2.0×10³ cells/well, and pre-cultured overnight. Here, as the medium, a CSC Complete Defined Medium (Cell systems) medium supplemented with 2% Culture Boost-R (50×) (Cell systems) and 0.2% Gentamycin/Amphotericin B (500×) (Gibco) was used. After pre-culture, a miR-203 inhibitor or a negative control thereof (QIAGEN), which was the same one as that in Test Example 5, was diluted with the medium, the dilution was mixed with HiPerFect Transfection Reagent (QIAGEN), and the mixture was incubated at 37° C. for 10 minutes, and added to the cells. Thereafter, the cells were cultured at 37° C. for 48 hours. The miR-203 inhibitor and a negative control thereof were added to cells so as to have a concentration of 50 nM. Moreover, the same procedures as in Test Example 6 were carried out to determine the live cell count. The graph collectively showing the results is shown in FIG. 4. In FIG. 4, the values are shown relative values where the cell count when treated with the negative control is defined as 1.

The effects of promoting cell proliferation by the miR-203 inhibitor could not be found in the normal human retinal microvascular endothelial cells.

Test Example 8

Figure 5:
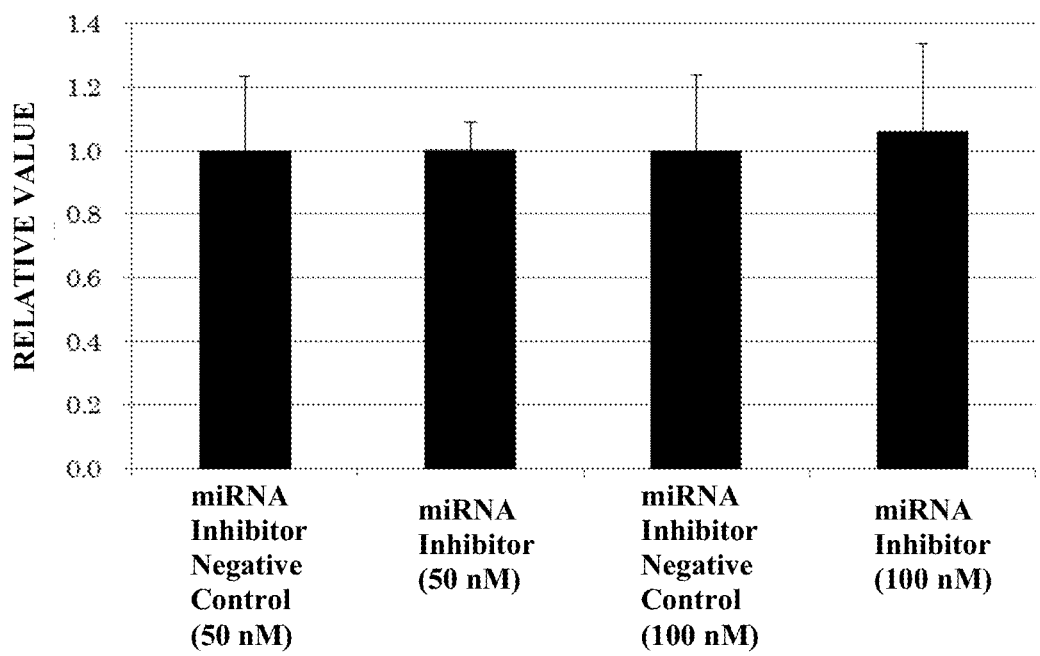
FIG. 5 is a graph showing the results of confirming the action of the miR-203 inhibitor on human trabecular meshwork cells (determination of live cell count) (n=5).

Introduction of miR-203 Inhibitor into Human Trabecular Meshwork Cells and Determination of Live Cell Count Human trabecular meshwork cells (ScienCell, Cat No. 6590) were seeded on a 96-well plate so as to have a density of $2.0 \times 10^3$ cells/well (30-50% confluent), and the cells were pre-cultured overnight. Here, as the medium, a Trabecular meshwork cell medium supplemented with 2% Fetal bovine serum (ScienCell), 1% Trabecular meshwork cell growth supplement (ScienCell), and 1% Penicillin/Streptomycin (ScienCell) was used. After pre-culture, a miR-203 inhibitor or a negative control thereof (QIAGEN), which was the same one as that in Test Example 5, was diluted with the medium, the dilution was mixed with HiPerFect Transfection Reagent (QIAGEN), and the mixture was incubated at room temperature for 10 minutes, and added to the cells. Thereafter, the cells were cultured at 37° C. for 48 hours. The miR-203 inhibitor and a negative control thereof were added to cells so as to have a concentration of 50 nM or 100 nM. Moreover, the same procedures as in Experiment Example 6 were carried out to determine the live cell count. The graph collectively showing the results is shown in FIG. 5. In FIG. 5, the values are expressed as relative values where the cell count when treated with the negative control is defined as 1.

It could be seen from FIG. 5 that the effects of promoting cell proliferation by the miR-203 inhibitor could not be found in the human trabecular meshwork cells.

The above results lead to the discussion as given below.

As a result of comparative studies of miRNAs in the tears and sera, miR-203 was found as one of the miRNAs relatively richly contained in the tears as compared to the sera of the monkey. The miR-203 analogue suppresses proliferation of human corneal epithelial cells and the miR-203 inhibitor promotes proliferation of human corneal epithelial cells. On the other hand, the miR-203 inhibitor did not promote proliferation of the human retinal microvascular endothelial cells and the human trabecular meshwork cells. These results suggested that the effects of promoting cell proliferation by the miR-203 inhibitor are cell-specific.

In addition, it could be seen that the miR-203 inhibitor shows the effects of promoting proliferation of the human corneal epithelial cells at a concentration as low as 50 nM or 100 nM.

From the above, it is considered that application of the miR-203 inhibitor as an active ingredient of a therapeutic agent for a corneal epithelial disorder, for example, an eye drop, or a method for treating a corneal epithelial disorder utilizing the miR-203 inhibitor is effective. Further, the miR-203 inhibitor can also be applied to an agent for promoting proliferation of corneal epithelial cells, a liquid culture medium for producing a corneal epithelial sheet, or a method for producing a corneal epithelial sheet.

Test Example 9

Introduction of miR-203 Inhibitor Having Sequence with Deletion of Nucleotides into Human Corneal Epithelial Cells and Determination of Live Cell Count The same procedures as in Test Example 5 were carried out to introduce each of a miR-203 inhibitor (sequence having two nucleotide deletion), a miR-203 inhibitor (sequence having six nucleotide deletion), a miR-203 inhibitor (sequence having fourteen nucleotide deletion), or a negative control thereof into the human corneal epithelial cells. Separately from these, the miR-203 inhibitor or a negative control thereof, which was the same one used in Test Example 5, was introduced into the human corneal epithelial cells in the same manner. Both the miR-203 inhibitor and negative controls thereof were added to the cells so as to have a concentration of 50 nM. Thereafter, the cells were cultured at 37° C. for 48 hours.

Here, as the miR-203 inhibitors having a sequence having deletion of nucleotides and a negative control thereof, the following ones were used.

Inhibitor Negative Control: one manufactured by EXIQON under trade name of "miRCURY LNA microRNA Inhibitor negative control A" was used.

miR-203 Inhibitor (Sequence Having Two Nucleotide Deletion): one manufactured by EXIQON under the trade name of "miRCURY LNA microRNA Inhibitor (hsa-miR-203)" was used. This is a synthetic single-stranded RNA consisting of 2 to 21 nucleotides (having two nucleotide deletion) of a complementary strand of the miR-203 sequence, in which an oxygen atom at 2' position and a carbon atom at 4' position of the ribonucleic acid are bridged via a methylene. The sequence of this inhibitor is shown in SEQ ID NO: 3 of the Sequence Listing.

miR-203 Inhibitor (Sequence Having Six Nucleotide Deletion): "hsa-mir-203a ASL-004" synthesized by Gene Design Inc. was used. This is a synthetic single-stranded RNA consisting of 7 to 22 nucleotides (six nucleotide deletion) of a complementary strand of the miR-203 sequence, in which an oxygen atom at 2' position and a carbon atom at 4' position of the ribonucleic acid are bridged via a methylene as shown by the following structural formula. The sequence of this inhibitor is shown in SEQ ID NO: 4 of the Sequence Listing. The nucleotides on the adjoining left of (L) shown below are bridged.

5'-G(L)UCC(L)UAA(L)ACA(L)UUUCA(L)C-3' miR-203 Inhibitor (Sequence Having Fourteen Nucleotide Deletion): "hsa-mir-203a ASL-005" synthesized by Gene Design Inc. was used. This is a synthetic single-stranded RNA consisting of 14 to 21 nucleotides (fourteen nucleotide deletion) of a complementary strand of the miR-203 sequence, in which an oxygen atom at 2' position and a carbon atom at 4' position of the ribonucleic acid are bridged via a methylene as shown by the following structural formula. The sequence of this inhibitor is shown in SEQ ID NO: 5 of the Sequence Listing. The nucleotides on the adjoining left of (L) shown below are bridged.

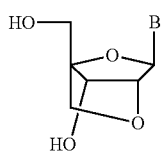

5'-A(L)C(L)A(L)U(L)U(L)U(L)C(L)A(L)-3'

Figure 6:
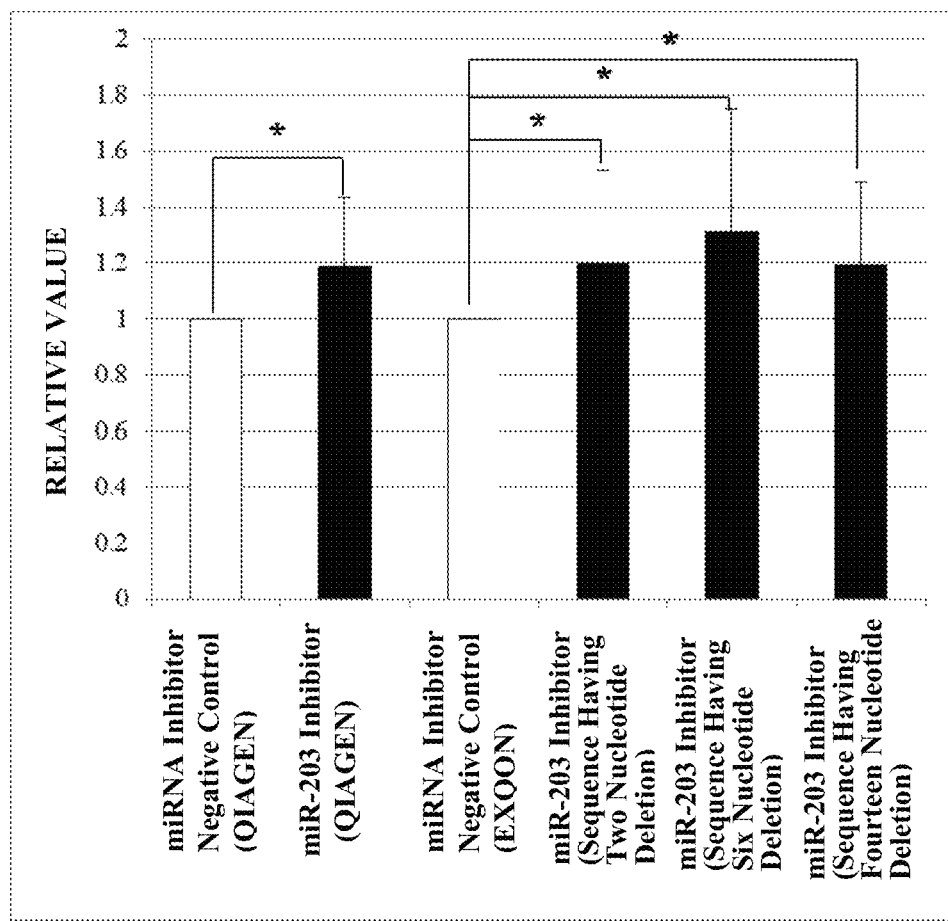
FIG. 6 is a graph showing the results confirming the action of a miR-203 inhibitor having a deletion of a nucleotide to human corneal epithelial cells (determination of live cell counts). In addition, the results of significance test (t-test, one side, significance level: 5%) are indicated ((n=6 or n=11).

As to the human corneal epithelial cells introduced with the miR-203 inhibitors and their negative controls, the live cell count was determined by the same procedures as in Test Example 6. The results are shown in FIG. 6. In FIG. 6, values are expressed as relative values where the cell count when treated with the negative control is defined as 1. All of the miR-203 inhibitor (sequence having two nucleotide deletion), the miR-203 inhibitor (sequence having six nucleotide deletion), and the miR-203 inhibitor (sequence having fourteen nucleotide deletion) were found to have significant effects of promoting proliferation of human corneal epithelial cells of the level equivalent to or higher than that of the miR-203 inhibitor without nucleotide deletions shown in the second lane from left of FIG. 6.

The above results lead to the followings.

The miR-203 inhibitors promoted proliferation of human corneal epithelial cells, even in a sequence having two nucleotide deletion, six nucleotide deletion or fourteen nucleotide deletion, without being limited to perfect complementary sequence to the sequence of miR-203. These results show that the miR-203 inhibitors are capable of inhibiting the action of miR-203 even with a partial complementary sequence of miR-203. Further, since the above effects are exhibited even in a sequence having fourteen nucleotide deletion, it is suggested that the desired effects are exhibited so long as a nucleotide sequence at least contains a nucleotide sequence as shown in SEQ ID NO: 5 of the Sequence Listing.

In the miR-203 inhibitor having a sequence of SEQ ID NO: 2 of the Sequence Listing which is shown to exhibit the above effects in Test Example 5, at least one hydroxyl group at 2' position of the ribonucleic acid is substituted with a methoxy group, from the viewpoint of stability as RNA. On the other hand, in the miR-203 inhibitor having any one of the sequences of SEQ ID NOs: 3 to 5 of the Sequence Listing which is shown to exhibit the above effects in Test Example 9, an oxygen atom at 2' position and a carbon atom at 4' position of the ribonucleic acid are bridged via a methylene, from the viewpoint of stability as RNA, the positions of the bridges are not the same.

As described above, exhibition of the desired effects regardless of the differences in the types of modifications in RNA suggests that the effects of the present invention are exhibited so long as it is an RNA having a given nucleotide sequence regardless of the presence or absence or positions of the modifications of RNA.

Formulation Example 1

Eye Drops

Eye drops shown below are prepared according to a conventional method.
The above miR-203 inhibitor (SEQ ID NO: 2 of the Sequence Listing):
0.001 g
Sodium dihydrogenphosphate dihydrate: 0.2 g
Sodium hydroxide: q. s.
Sodium chloride: 0.8 g
Benzalkonium chloride: 0.005 g
Sterilized purified water: q. s.
Entire volume 100 mL (pH 7.0)

Test Example 10

Studies of Promoting Action on Corneal Epithelial Wound Healing

1. Animal Used
Male Japanese white rabbits (KITAYAMA LABES CO., LTD.) are used. The use of the experimental animal complies with the International Guiding Principles for Biomedical Research involving Animals. In the group administered with a miR-203 inhibitor, eye drops containing a miR-203 inhibitor shown in the above Formulation Example 1 are used. In the group administered with a basal agent which is a control, an eye drops basal agent which is identical to that of the eye drops of Formulation Example 1 except that the miR-203 inhibitor is not contained is used.
2. Experimental Methods
1) Corneal Epithelial Scraping
The animal is subjected to a systemic anesthesia by intramuscular injection (1 mL/kg) containing a 3:1 mixed solution of 5% ketamine (500 g of Ketalar (registered trademark) for intramuscular injection, Daiichi Sankyo Propharma Co. Ltd.) and 2% xylazine (2% injection solution of Selectar (registered trademark); Bayer Yakuhin Ltd.). Thereafter, 0.4% oxybuprocaine hydrochloride eye drops (0.4% eye drops of Benoxil (registered trademark): Santen Pharmaceutical CO., Ltd.) are instilled, and eye ball was dislocated. A mark having a diameter of 10 mm is stamped on the corneal epithelium in the central part using a trephine having a diameter of 10 mm, and the entire corneal epithelial layer within the stamped circumference is scraped off using a handy rooter under a stereomicroscope. After scraping, the corneal surface is washed with physiological saline (OTSUKA PHARMACEUTICAL FACTORY, INC.), the eye ball is placed back into the orbit to complete the corneal epithelial scraping treatment.
2) Administration
Eye drops containing a miR-203 inhibitor or eye drops basal agent is each instilled into the treated eye with a micropipette in an amount of 50 μL per instillation, twice a day on the day of corneal epithelial scraping, and four times a day from the next day to the termination of the test.
3) Evaluation
Defining the time point at which the corneal epithelial scraping of all the individuals is terminated as a test initiation time (0th hour), the restoration of the corneal epithelium is evaluated by quantifying areas of the corneal epithelial defect after 40, 48, 56, or 64 hours later. Concretely, a 0.1% fluorescein sodium (Wako Pure Chemical Industries, Ltd.) solution is instilled into the treated eye at each time point in an amount of 10 μL, and an anterior ocular segment of the animal is immediately photographed using a slit lamp with a blue filter, whereby the fluorescein-stained corneal epithelial defective region is recorded. The developed photograph is stored as digital images on a computer, and the areas of the fluorescein-stained corneal epithelial defect are measured with an image analysis software (Image-Pro Plus). The proportion of the remaining corneal epithelial defect at each time point is compared between the group administered with the basal agent and the group administered with the miR-203 inhibitor. As a result of the examination, it is judged that a risk rate of less than 5% is significant.

Formulation Example 2

Liquid Culture Medium

To a DMEM/Ham's F12 mixed medium (mixed volume ratio: 1:1) are added 10% FBS, insulin (5 µg/mL), cholera toxin (0.1 nM), penicillin streptomycin (50 IU/mL), human recombinant epidermal growth factor (EGF) (10 ng/mL), 50 nM miR-203 inhibitor mentioned above (SEQ ID NO: 2 of the Sequence Listing) to prepare a liquid culture medium.

A corneal epithelial sheet is produced using a liquid culture medium mentioned above in place of a medium described in paragraph 0041 of Japanese Unexamined Patent Publication No. 2006-003818.

The entire teachings of all the patents, published patent applications, and referential publications cited in the present specification are incorporated herein by reference.

INDUSTRIAL APPLICABILITY

The present invention is utilizable in the fields of a therapeutic agent for a corneal epithelial disorder for mammals, or a method for treating a corneal epithelial disorder, or a miR-203 inhibitor for treatment of a corneal epithelial disorder.

SEQUENCE LISTING FREE TEXT

SEQ ID NO: 1 of the Sequence Listing is a nucleotide sequence of miR-203.

SEQ ID NO: 2 of the Sequence Listing is a nucleotide sequence of an antisense nucleic acid against miR-203.

SEQ ID NO: 3 of the Sequence Listing is a nucleotide sequence of an antisense nucleic acid against miR-203, which is a sequence of positions 2 to 21 of the sequence of SEQ ID NO: 2 of the Sequence Listing.

SEQ ID NO: 4 of the Sequence Listing is a nucleotide sequence of an antisense nucleic acid against miR-203, which is a sequence of positions 7 to 22 of the sequence of SEQ ID NO: 2 of the Sequence Listing.

SEQ ID NO: 5 of the Sequence Listing is a nucleotide sequence of an antisense nucleic acid against miR-203, which is a sequence of positions 14 to 21 of the sequence of SEQ ID NO: 2 of the Sequence Listing.

The invention claimed is:

1. A method for treating a corneal epithelial disorder, comprising the step of administering a therapeutically effective amount of an miR-203 inhibitor to an individual in need of treatment for a corneal epithelial disorder,
    wherein the miR-203 inhibitor is an RNA antisense nucleic acid against miR-203,
    wherein the miR-203 inhibitor has an action of promoting proliferation of corneal epithelial cells by hybridizing to miR-203 and suppressing an action of miR-203, and
    wherein the corneal epithelial disorder is a disease accompanying a wound or defect of corneal epithelial cells.

2. The method according to claim 1, wherein the corneal epithelial disorder is selected from the group consisting of Sjögren syndrome, Stephens-Johnson syndrome, keratoconjunctivitis sicca, diabetic keratopathy, a post-operation disorder, drug use, trauma, corneal ulcer, meibomianitis, symptoms caused by wearing contact lenses, vernal catarrh, atopic keratoconjuctivitis, superficial punctate keratitis and corneal epithelial erosion.

3. The method according to claim 1, wherein the antisense nucleic acid is an RNA comprising a nucleotide sequence shown in any one of SEQ ID NOs: 2 to 5.

4. The method according to claim 1, wherein the antisense nucleic acid is an RNA consisting of a nucleotide sequence having substitution, deletion, addition and/or insertion of one to three nucleotides in the nucleotide sequence shown in any one of SEQ ID NOs: 2 to 5.

5. The method according to claim 1, wherein the antisense nucleic acid is
    (1) an RNA consisting of a nucleotide sequence having substitution and/or deletion of one nucleotide at a 5' terminal and/or one nucleotide at a 3' terminal of the nucleotide sequence, in the nucleotide sequence shown in any one of SEQ ID NOs: 2 to 5, or
    (2) an RNA consisting of a nucleotide sequence having addition of one nucleotide to a nucleotide at a 5' terminal and/or to a nucleotide at a 3' terminal of the nucleotide sequence, in the nucleotide sequence shown in any one of SEQ ID NOs: 2 to 5.

6. The method according to claim 1, wherein the antisense nucleic acid is an RNA consisting of a nucleotide sequence shown in any one of SEQ ID NOs: 2 to 5.

7. The method according to claim 6, wherein a hydroxyl group at a 2' position of all the ribonucleic acids constituting the RNA is substituted with a methoxy group, or an oxygen atom at a 2' position and a carbon atom at a 4' position of at least one ribonucleic acid constituting the RNA are bridged via a methylene.

8. A method for promoting proliferation of corneal epithelial cells, comprising:
    administering an effective amount of an miR-203 inhibitor to an individual in need of promoting proliferation of corneal epithelial cells,
    wherein the miR-203 inhibitor is an RNA antisense nucleic acid against miR-203,
    wherein the miR-203 inhibitor has an action of promoting proliferation of corneal epithelial cells by hybridizing to miR-203 and suppressing an action of miR-203.

9. The method according to claim 8, wherein the antisense nucleic acid is an RNA comprising a nucleotide sequence shown in any one of SEQ ID NOs: 2 to 5.

10. The method according to claim 8, wherein the antisense nucleic acid is an RNA consisting of a nucleotide sequence having substitution, deletion, addition and/or insertion of one to three nucleotides in the nucleotide sequence shown in any one of SEQ ID NOs: 2 to 5.

11. The method according to claim 8, wherein the antisense nucleic acid is
    (1) an RNA consisting of a nucleotide sequence having substitution and/or deletion of one nucleotide at a 5' terminal and/or one nucleotide at a 3' terminal of the nucleotide sequence, in the nucleotide sequence shown in any one of SEQ ID NOs: 2 to 5, or
    (2) an RNA consisting of a nucleotide sequence having addition of one nucleotide to a nucleotide at a 5' terminal and/or to a nucleotide at a 3' terminal of the nucleotide sequence, in the nucleotide sequence shown in any one of SEQ ID NOs: 2 to 5.

12. The method according to claim 8, wherein the antisense nucleic acid is an RNA consisting of a nucleotide sequence shown in any one of SEQ ID NOs: 2 to 5.

13. The method according to claim 12, wherein a hydroxyl group at a 2' position of all the ribonucleic acids constituting the RNA is substituted with a methoxy group, or an oxygen atom at a 2' position and a carbon atom at a 4' position of at least one ribonucleic acid constituting the RNA are bridged via a methylene.

* * * * *

```
                              SEQUENCE LISTING

<160> NUMBER OF SEQ ID NOS: 5

<210> SEQ ID NO 1
<211> LENGTH: 22
<212> TYPE: RNA
<213> ORGANISM: Homo sapiens
<223> OTHER INFORMATION: Sequence of miR-203

<400> SEQUENCE: 1
gugaaauguu uaggaccacu ag                                                  22

<210> SEQ ID NO 2
<211> LENGTH: 22
<212> TYPE: RNA
<213> ORGANISM: Artificial Sequence
<220> FEATURE:
<223> OTHER INFORMATION: antisense oligonucleotide

<400> SEQUENCE: 2
cuaguggucc uaaacauuuc ac                                                  22

<210> SEQ ID NO 3
<211> LENGTH: 20
<212> TYPE: RNA
<213> ORGANISM: Artificial Sequence
<220> FEATURE:
<223> OTHER INFORMATION: antisense oligonucleotide

<400> SEQUENCE: 3
uagugguccu aaacauuuca                                                     20

<210> SEQ ID NO 4
<211> LENGTH: 16
<212> TYPE: RNA
<213> ORGANISM: Artificial Sequence
<220> FEATURE:
<223> OTHER INFORMATION: antisense oligonucleotide

<400> SEQUENCE: 4
guccuaaaca uuucac                                                         16
```

```
<210> SEQ ID NO 5
<211> LENGTH: 8
<212> TYPE: RNA
<213> ORGANISM: Artificial Sequence
<220> FEATURE:
<223> OTHER INFORMATION: antisense oligonucleotide

<400> SEQUENCE: 5 acauuuca                                                                8
```